US00PP10737P

United States Patent [19]

Olesen et al.

[11] Patent Number: Plant 10,737

[45] Date of Patent: Dec. 29, 1998

[54] MINIATURE ROSE PLANT NAMED 'POULEZY'

[75] Inventors: L. Pernille Olesen; Mogens N. Olesen, both of Fredensborg, Denmark

[73] Assignee: Poulsen Roser ApS, Fredensborg, Denmark

[21] Appl. No.: 833,507

[22] Filed: Apr. 7, 1997

[51] Int. Cl.[6] ..... A01H 5/00

[52] U.S. Cl. ..... Plt./8.1

[58] Field of Search ..... Plt./8.1, 7.1

[56] References Cited

U.S. PATENT DOCUMENTS

P.P. 6,822 5/1989 Moore ..... Plt./8.1

P.P. 8,941 10/1994 Olesen et al. ..... Plt./8.1

P.P. 9,280 9/1995 Olesen et al. ..... Plt./8.1

OTHER PUBLICATIONS

UPOV–ROM, 1997 Apr., Plant Variety Database, GTI Jouve Retrieval Software, citation for 'POULezy'.

*Primary Examiner*—Howard J. Locker

[57] ABSTRACT

A new white miniature rose plant which has abundant non-fading flowers and very good keepability. The variety successfully propagates from softwood cuttings and is suitable for year round production in commercial glasshouses. This new and distinct variety has shown to be uniform and stable in the resulting generations from such asexual propagation.

2 Drawing Sheets

SUMMARY OF THE INVENTION

The present invention constitutes a new and distinct variety of miniature rose plant which originated from a controlled crossing between unnamed seedlings in a cultivated area. The two parents were crossed during the summer of 1993 and the resulting seed was planted during December, 1993 in a controlled environment. The new variety is named 'POULezy'.

The objective of the hybridization of this rose variety for commercial greenhouse culture was to create a new and distinct variety with:

1. Uniform and abundant flowers with excellent keepability;
2. Attractive long lasting foliage and compact growth,
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type and distinguish 'POULezy' from all other varieties of which we are aware.

The seeds from the hybridization were germinated in February, 1994 and evaluations were conducted of the resulting rose plants in a controlled environment.

'POULezy' was selected by L. Pernille and Mogens N. Olesen in their rose development program in Fredensborg, Denmark in June, 1994.

Asexual reproduction of 'POULezy' by cuttings as well as by traditional budding was first done by L. Pernille and Mogens N. Olesen in August, 1994. These initial and subsequent propagations have demonstrated that the characteristics of 'POULezy' are true to type and are transmitted from one generation to the next.

BRIEF DESCRIPTION OF THE DRAWINGS

The accompanying color illustrations show as true as is reasonably possible to obtain in color photographs of this type, the typical characteristics of the buds, flowers, leaves, stems, and a plant of 'POULezy'. Specifically illustrated in SHEET 1: 1. Stem or entire plant showing branching and the attachment of leaves, buds, and peduncles; 2. Flower bud, partially opened bud, and open bloom; 3. Flower petals, detached; 4. Sepals, receptacle, and pedicel; 5. Flowering stem as well as a bare stem exhibiting thorns; 6. Leaves.

Specifically illustrated in SHEET 2 is an entire blooming plant in a 10 cm pot.

DETAILED DESCRIPTION OF THE VARIETY

The following is a detailed description of 'POULezy' as observed in its growth in glasshouses in Fredensborg, Denmark and Half Moon Bay, Calif. and in field nursery in Applegate, Oreg. Descriptions were made from plants treated with growth regulators normally used in the greenhouse production process.

The growth regulator Paclobutrazol was applied to 30 ppm weekly for three weeks beginning at a plant age of 8 weeks. The peduncle lengths mentioned may actually be shorter and the foliage color several shades darker than on untreated specimens. Color references are made using The Royal Horticultural Society (London, England) Colour Chart, 1995.

For a comparison, the nearest existing rose variety is 'POULbian', a patented variety described and illustrated in U.S. Plant Pat. No. 9,280 and issued on Sep. 12, 1995. Chart 1 lists two physical characteristics of 'POULezy' and the comparison variety.

CHART 1

| Characteristic | 'POULezy' | 'POULbian' |
|---|---|---|
| Number of blooms | less abundant | more abundant |
| Petal size | small to medium | very small |

Parents: Unnamed seedling×unnamed seedling.

Classification:

*Botanical.*—*Rosa hybrida.*

*Commercial.*—Miniature.

Flower and Flower Bud

Blooming cycle: Recurrent.

Flower bud:

*Size.*—12–14 mm in length when petals are just beginning to crack open.

*Bud form.*—Pointed ovoid.

*Bud color.*—R.H.S. 155 B of the White Color Group at ¼ opening.

*Sepals.*—R.H.S. 139 C of the Green Group. Weak foliaceous appendages on three of the five sepals. Surfaces of sepals moderately pubescent with glandular hairs present on margins and the outer surface of sepals.

*Peduncle.*—Surface: Covered in thickened hairs and small prickles. Length: 25–30 mm average length. Color: R.H.S. 143 A of the Green Group. Prickles: Few.

*Receptacle.*—Surface: Smooth, with very fine small hairs. Shape: Urn shaped. Size: Small to medium. 5 mm×6 mm. Color: R.H.S. 143 A of the Green Group.

*Borne.*—Singly, several together, in flat clusters of 2 to 4 flowers.

Flower bloom:

*Diameter.*—Small 40–45 mm. on average.

*Form.*—Upon opening, ovoid. Completely open a flattened convex, with outer petals curling backwards.

*Petalage.*—Double. Average range: 30–40 petals.

*Color.*—Upon and after opening, the upper surface is R.H.S. 155 B of the White Color Group. Upon and after opening, the reverse side is R.H.S. 155 B of the White Color Group. A small petal spot R.H.S. 2 D of the Yellow Color Group exists on the inner and outer side of the petal base.

*Reflex.*—Almost all petals reflex backwards, with most edges quilling.

*Variations.*—None. Some petal edges with weak undulations.

*Fragrance.*—Moderate.

*Duration.*—As a pot plant, flowers last from 15–18 days. As a cut flower flowers last 8–12 days.

Reproductive organs:

*Pollen.*—Golden Yellow Group 13B.

*Anthers.*—Size: Medium. Many, arranged regularly around styles. Color: Golden yellow Group 13C.

*Filaments.*—Color: Green-Yellow Group 1C.

*Stigmas.*—Slightly superior in location in reference to anthers.

*Styles.*—Color: Green-Yellow Group 1D.

Plant

Plant growth: Vigorous and upright. When grown as a 10 cm pot plant, the average height of the plant itself is 18–22 cm and the average width is 18–22 cm. When grown as a nursery plant on its own roots the average plant height is 25–35 cm and the average plant width is 30–40 cm.

Stems:

*Color.*—Young wood: Green Group 138A. Older wood: Green Group 137D.

*Thorns.*—Incidence: Very few thorns. Size: Average length: 2 mm. Color: Orange-White Group 159A. Shape: Linear.

*Bark.*—Young wood: Smooth. Older wood: Smooth.

Plant foliage:

*Normal number of leaflets on average leaves.*—5 leaflets.

*Leaf size.*—Small. 45×60 mm.

*Abundance.*—Average.

*Color, mature foliage.*—Upper leaf surface: Dark green. R.H.S. 147 A of the Green Color Group. Lower leaf surface: Medium. R.H.S. 138 B of the Green Color Group.

*Color juvenile foliage.*—Upper lear surface is Green Group 143A. Lower leaf surface is Green Group 139C.

Plant leaves and leaflets:

*Stipules.*—Present. To 8 mm. Bearded. Thickened hairs present. Green Group 138B.

*Petiole.*—Length: 10–12 mm. Underneath: Without prickles. Color: Green Group 138B.

*Edge.*—Finely serrated.

*Shape.*—Leaflets are ovate.

*Leaflets.*—Number: 5.

*Other.*—Semi-matte finish. Thick texture. Leaf rachis is Green Group 138B.

Disease resistance: Resistant to rust, black spot, and Botrytis under normal growing conditions in Half Moon Bay, Calif. and Fredensborg, Denmark.

We claim:

1. A new and distinct variety of rose plant of the miniature class, substantially as herein illustrated and described, as a distinct and novel rose variety due to its abundant flowers with good keepability, attractive long lasting foliage and compact growth, year round flowering under glasshouse conditions, suitability for production from softwood cuttings in pots, durable flowers and foliage which make the variety suitable for distribution in the floral industry.

* * * * *

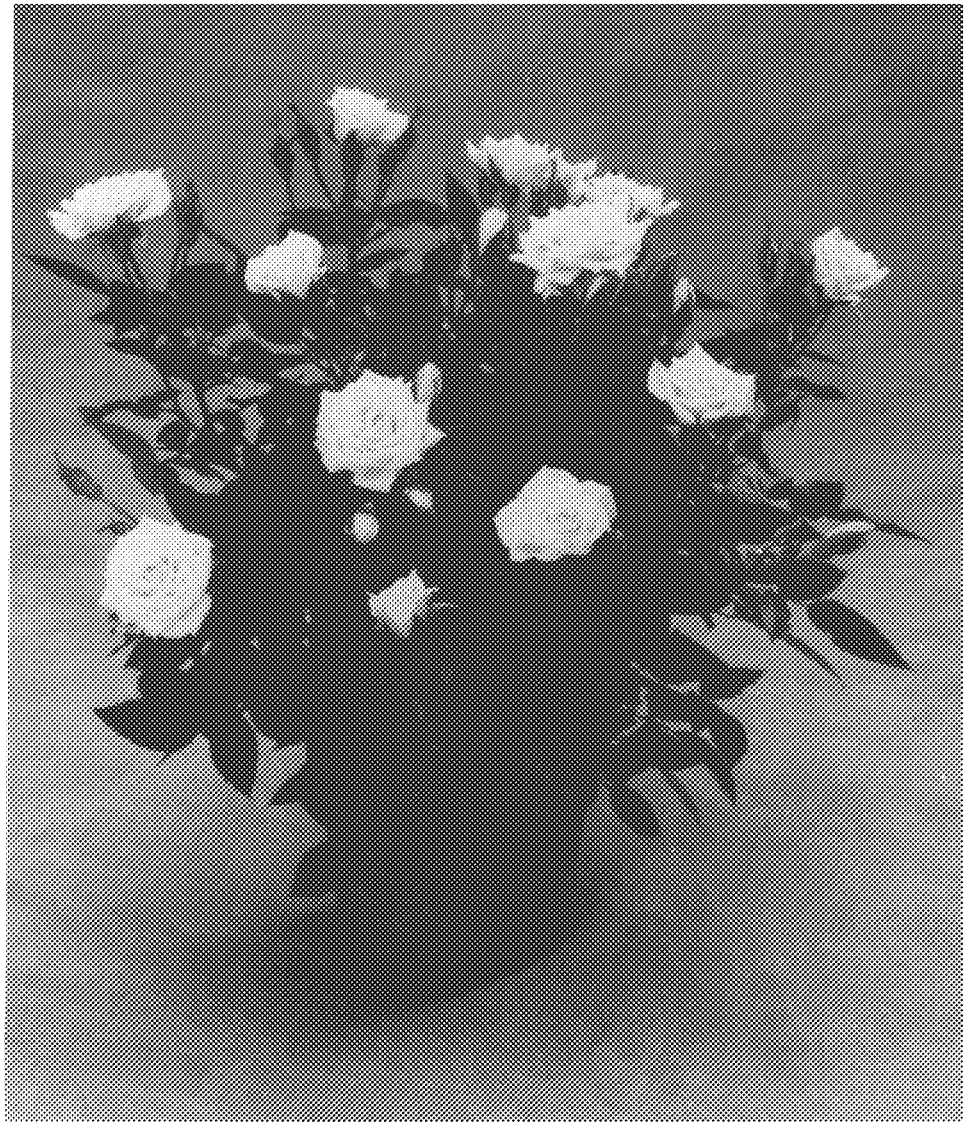

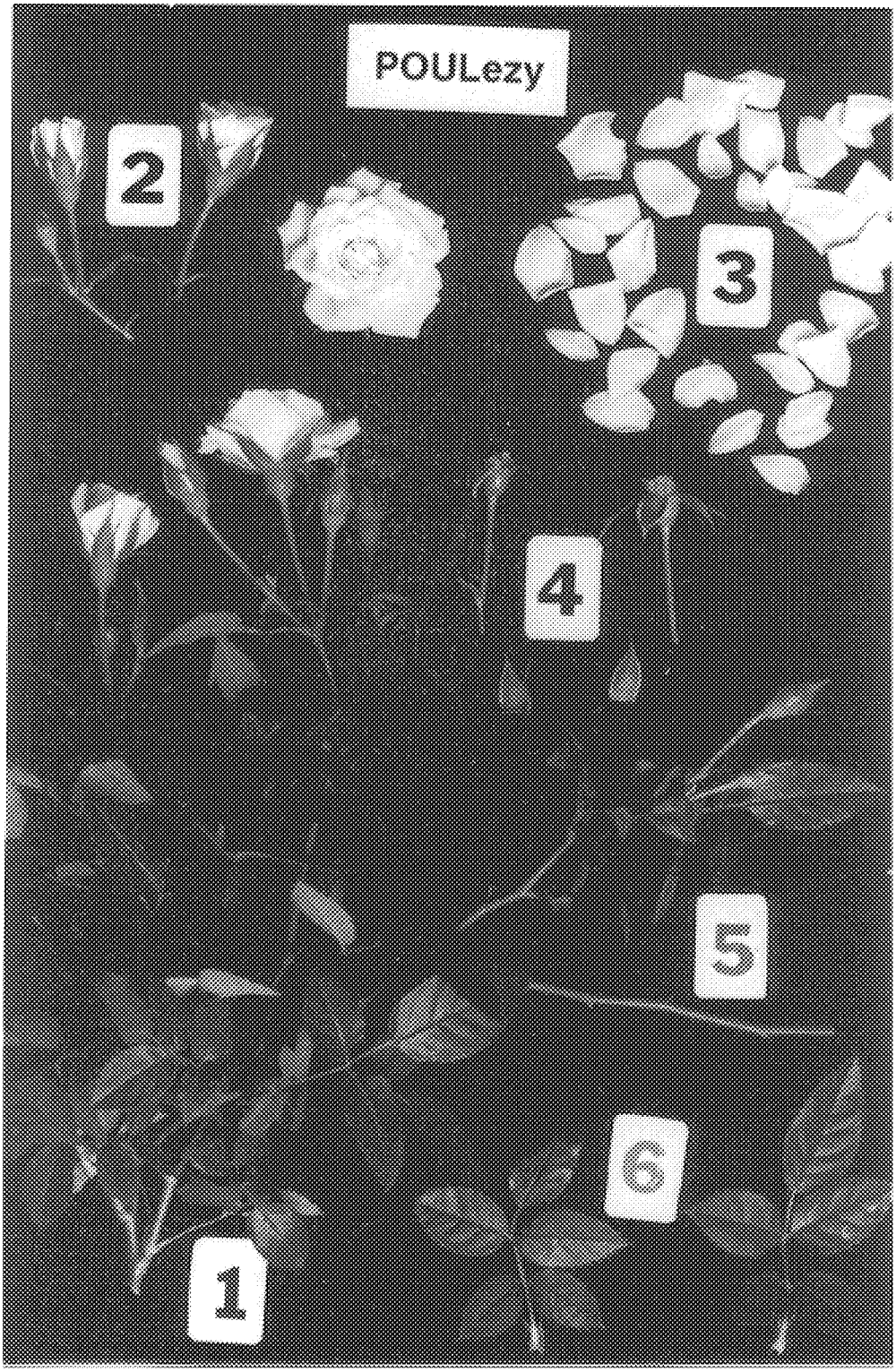
POULezy
2
3
4
5
6
1